United States Patent [19]

Kise et al.

[11] Patent Number: 5,182,198

[45] Date of Patent: Jan. 26, 1993

[54] PROCESS FOR PREPARING (+)-HOMOPILOPIC ACID

[75] Inventors: Shoichi Kise; Mikio Hayashida; Aiichiro Ori; Junzou Hiratsuka, all of Yamaguchi; Hideaki Yamada, Kyoto, all of Japan

[73] Assignee: Mitsui Petrochemical Industries, Ltd., Tokyo, Japan

[21] Appl. No.: 614,132

[22] Filed: Nov. 16, 1990

[30] Foreign Application Priority Data

Nov. 22, 1989 [JP] Japan .................................. 1-302273

[51] Int. Cl.$^5$ .................. C12P 17/04; C12N 9/18; C12N 9/20; C12R 1/845
[52] U.S. Cl. .................................. 435/126; 435/118; 435/197; 435/198; 435/280; 435/822; 435/839; 435/840; 435/939
[58] Field of Search ............... 549/323, 322; 435/126, 435/119, 118, 822, 939, 839, 840, 197, 198, 280

[56] References Cited

FOREIGN PATENT DOCUMENTS 0325954 2/1989 European Pat. Off. .

OTHER PUBLICATIONS

CA.89:24125h Zvonkova et al., "Homopilopic Acid" USSR 589,243 Apr. 1976 vol. 89 (1978).
CA78:43245m Zav'yalov et al., "Homoisopilopic Acid" USSR 352,892 Sep. 1972.
CA 99886x DeGraw Tetrahed Lts. 1972 '28 (4)967-72 vol. 76 (1972).
CA 51497z Chumachenko et al., vol. 69 (1968) SSSR 1968 178(6) 1352-5.
J. I. DeGraw et al., J. Pharm. Sci., 64:1700-1701 (1975).
DeGraw, Tetrahedron, vol. 28, 967-972 (1972).

*Primary Examiner*—Herbert J. Lilling
*Attorney, Agent, or Firm*—Birch, Stewart, Kolasch and Birch

[57] ABSTRACT

A process for preparing (+)-homopilopic acid and the salts thereof which comprises hydrolyzing a mixture of (+)-homopilopic acid ester of the general formula (I):

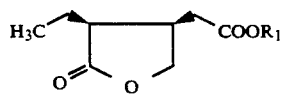

[I]

wherein $R_1$ denotes straight or branched $C_1$-$C_{10}$ hydrocarbon, and (−)-homopilopic acid ester of the general formula (II):

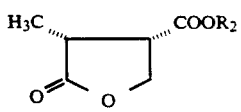

[II]

wherein $R_2$ denotes straight or branched $C_1$-$C_{10}$ hydrocarbon, in the presence of a microorganism belonging to the genus Arthrobacter, Aspergillus, Escherichia, Cunninghamella, Xanthomonas, Candida, Pseudomonas, Serratia, Cellulomonas, Nocardia, Bacillus, Brevibacterium, Flavobacterium, Mycobacterium, Rhizomucor, Rhodotorula or Rhodococcus, or a treated matter thereof.

23 Claims, 1 Drawing Sheet

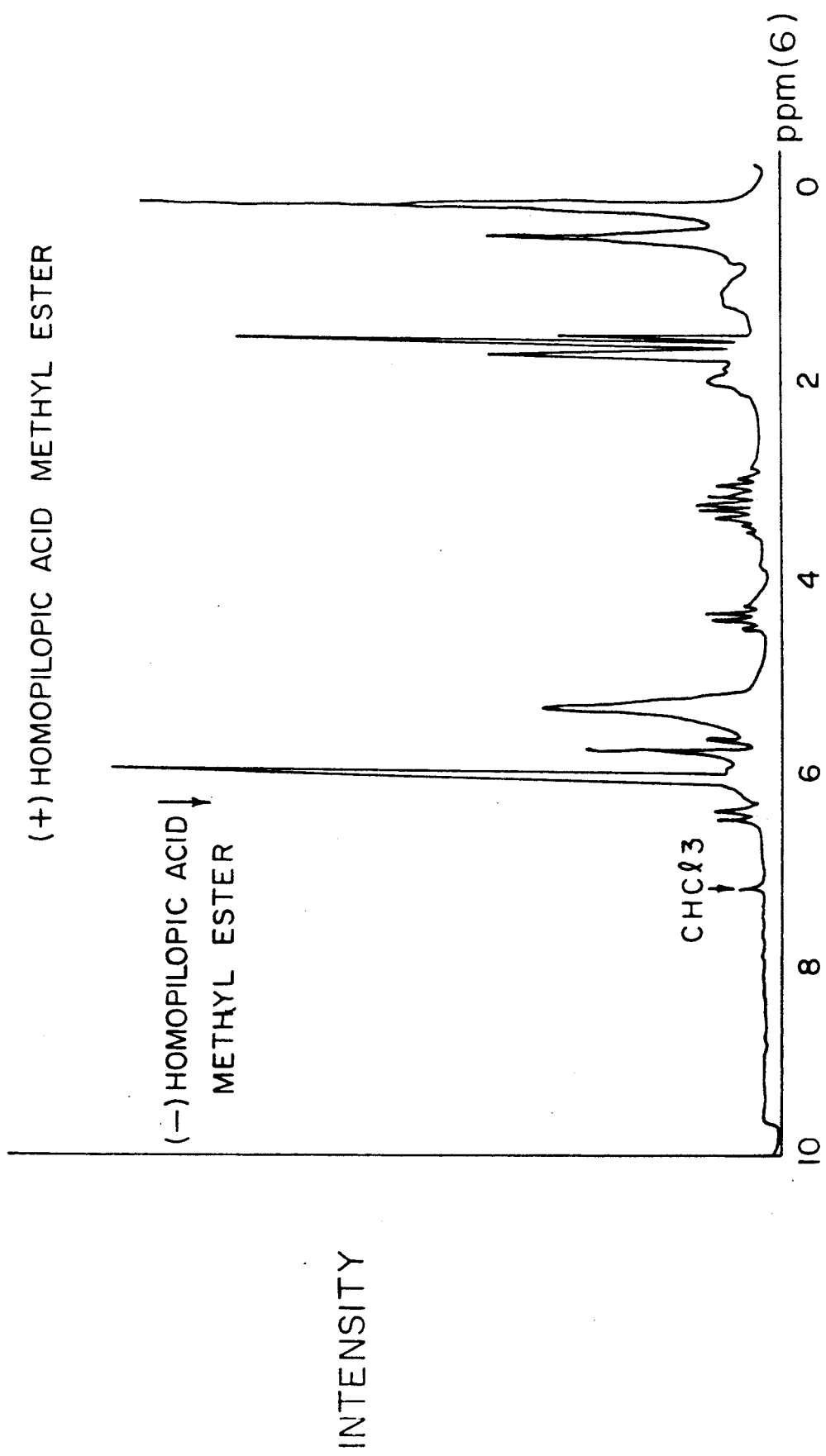

PROCESS FOR PREPARING (+)-HOMOPILOPIC ACID

The present invention relates to a process for preparing (+)-homopilopic acid and the salts thereof. These compounds are useful as intermediates for preparing (+)-pilocarpine hydrochloride, which is a valuable medicament for the treatment of glaucoma.

PRIOR ART

Presently, the compound (+)-pilocarpine hydrochloride of the formula (III):

is obtained by extracting the leaves of *Pilocarpus jaborandi* indigenous to Brazil and other countries. Such method, however, has a problem in that the supply of naturally growing raw material is susceptible to climatic influences, and is difficult to provide constantly.

When (+)-pilocarpine hydrochloride is prepared by synthesis, it is prepared by hydrolyzing a mixture of (+)-homopilopic acid ester and (−)-homopilopic acid ester (said mixture will be referred to as (±)-homopilopic acid ester, hereinafter) under strongly acidic conditions, optically resolving the resulting mixture of (+)-homopilopic acid of the formula (IV):

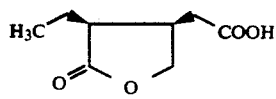

and (31)-homopilopic acid of the formula (V):

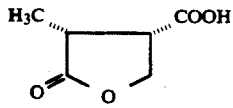

(said mixture will be referred to as (±)-homopilopic acid, hereinafter), using d-α-methylbenzylamine to remove (−)-homopilopic acid, and converting the (+)-homopilopic acid to (+)-pilocarpine hydrochloride (J. I. DeGraw et. al., J. Pharm. Sci., 64:1700–1701, (1975)).

PROBLEMS TO BE SOLVED BY THE INVENTION

The hydrolysis of (±)-homopilopic acid ester under strongly acidic conditions as in the above mentioned prior art causes the cleavage of the lactone ring, and the yield of (+)-homopilopic acid is low. Also, in the hydrolysis under alkaline conditions, the lactone ring is cleaved and the yield decreases considerably. Therefore, the object of the present invention is to provide a process for preparing (+)-homopilopic acid efficiently and in high yield.

MEANS FOR SOLVING THE PROBLEM

The inventors have found that (+)-homopilopic acid can be prepared efficiently and in high yield by conducting the hydrolysis under mild conditions using a microorganism or an enzyme in order to prevent the cleavage of the lactone ring.

SUMMARY OF THE INVENTION

The present invention relates to (1) a process for preparing (+)-homopilopic acid and salts thereof, which comprises hydrolyzing (±)-homopilopic acid ester, namely a mixture of the compounds of the general formulas (I) and (II) wherein $R_1$ and $R_2$ denote straight or branched $C_1$–$C_{10}$ hydrocarbons, using a microorganism belonging to the genera Arthrobacter, Aspergillus, Escherichia, Cunninghamella, Xanthomonas, Candida, Pseudomonas, Serratia, Cellulomonas, Nocardia, Bacillus, Brevibacterium, Flavobacterium, Mycobacterium, Rhizomucor, Rhodotorula or Rhodococcus, or a treated matter thereof (Process 1).

Another aspect of the invention is to provide (2) a process for preparing (+)-homopilopic acid and salts thereof, which comprises hydrolyzing (±)-homopilopic acid ester, namely a mixture of the compounds of the general formula (I) and (II) wherein $R_1$ and $R_2$ denote straight or branched $C_1$–$C_{10}$ hydrocarbons, using at least one enzyme selected from the group consisting of a lipase, an esterase, a cholesterol esterase, and a lipoprotein lipase (Process 2).

A further aspect of the present invention is to provide (3) a process for preparing (+)-homopilopic acid and salts thereof, which comprises hydrolyzing a mixture of (+)-homopilopic acid ester of the general formula (I) wherein $R_1$ denotes a straight or branched $C_1$–$C_{10}$ hydrocarbon, and (−)-homopilopic acid ester of the general formula (II) wherein $R_2$ denotes a straight or branched $C_1$–$C_{10}$ hydrocarbon using either a hydrolase selected from the group consisting of a lipase, an esterase, and a cholesterol esterase, or a microorganism belonging to the genus Brevibacterium, Escherichia or Rhodotorula, or a treated matter thereof, recovering the unreacted (+)-homopilopic acid ester, thereafter hydrolyzing said unreacted (+)-homopilopic acid ester using either a hydrolase selected from the group consisting of a lipase and a esterase, or a microorganism belonging to the genus Aspergillus, Escherichia, Xanthomonas, Candida, Pseudomonas, Serratia, Cellulomonas, Nocardia, Bacillus, Flavobacterium, Brevibacterium, Mycobacterium, Rhizomucor or Rhodococcus, or a treated matter thereof (Process 3).

FIG. 1 shows the NMR spectrum of the methyl ester of the product of Example 37 in CDCl$_3$ in the presence of 0.5 equivalent of Eu (hfc)$_3$.

The invention will be described in detail hereinafter.

Suitable as $R_1$ and $R_2$ are straight or branched $C_1$–$C_{10}$ hydrocarbons, typically methyl, ethyl, isopropyl, t-butyl and octyl.

Suitable microorganisms for Process 1 of the present invention are *Arthrobacter globiformis* IFO 12136, *Aspergillus sojae* IAM 2703, *Aspergillus terreus* IAM 2179, *Escherichia coli* IFO 3366, *Cunninghamella echinulata* IFO 4443, *Xanthomonas campestris* IFO 13303, *Xanthomonas oryzae* IFO 3510, *Candida utilis* IFO 4961, *Pseudomonas aeruginosa* IAM 1275, *Serratia plymuthica* JCM 1244, *Cellulomonas turbata* FERM P-9059, *Nocardia erythropolis* IAM 1484, *Nocardia opaca* IAM 12123, *Nocardia corallina* IAM 12121, *Nocardia rubropertincta* JCM 3204, *Bacillus subtilis* IFO 3108 *Flavobacterium lutescens* IFO 3084 *Brevibacterium ketoglutamicum* ATCC 15588, *Mycobacterium rhodochrous* IFO 13161, *Rhizomucor miehei* IFO 9740, *Rhodococcus erythropolis* IFO 12682, *Rhodotorula rubra* IFO 0383, and the like.

*Escherichia coli* IFO 3366, *Bacillus subtilis* IFO 3108, and *Rhizomucor miehei* IFO 9740 are available from the Institute for Fermentation, 17-85, Juso-honmachi 2-chome, Yodogawa-ku, Osaka 532, Japan. *Nocardia rubropertincta* JCM 3204 (FERM BP-3641) is available from the Fermentation Research Institute, Agency of Industrial Science and Technology, Ministry of International Trade and Industry, 1-3, Higashi 1-chome, Tsukuba-shi, Ibaraki-ken 305, Japan under the terms of the Budapest Treaty. *Brevibacterium ketoglutamicum* ATCC 15588 is available from the American Type Culture Collection, 12301 Parklawn Drive, Rockville, Md. 20852-1776.

Though Process 1 of the present invention may be carried out by culturing one of these microorganisms in a medium containing a ($\pm$)-homopilopic acid ester, it is preferably conducted by culturing these microorganisms in a medium containing yeast extract, peptone, glucose, mineral salts, etc., at 20°–37° C. for a period of 1 day to 1 week, and contacting the resultant culture, cells, the supernatant, or a treated matter thereof such as crude enzyme solution obtained by disrupting the cells in the culture, with ($\pm$)-homopilopic acid ester.

For example, (+)-homopilopic acid may be obtained in an aqueous solution by adding 0.1–30%, preferably 0.5–10% by weight of ($\pm$)-homopilopic acid ester to phosphate buffer or Tris-HCl, pH 5–9 preferably pH 6.0–8.0, containing said culture, cells, the supernatant or treated matter thereof, and shaking the mixture at 20°–37° C. for 2 to 100 hours. The pH value of the reaction solution decreases as the hydrolysis proceeds and therefore, it is preferable to add 0.5N sodium hydroxide, sat. sodium hydrogen carbonate or sat. sodium carbonate in order to neutralize and adjust the pH. After the reaction, (+)-homopilopic acid can be recovered and purified from the reaction mixture by conventional solvent-extraction, ion exchange chromatography, etc. Specifically, the unreacted starting esters may be removed by extracting with diethyl ether. The pH of the remaining aqueous layer is adjusted to 2–4 with 2N HCl or 2N $H_2SO_4$, and NaCl is added to saturation. To this mixture, an equal volume of ethyl acetate is added, stirred vigorously and centrifuged to recover the ethyl acetate layer which is then dried under reduced pressure to give raw crystals of homopilopic acid. The ratio of (+)-homopilopic acid and (−)-isomer varies from 91:9 to 25:75, depending on the type of the microorganism employed. Preferably, *Rhizomucor miehei* IFO 9740 is used to obtain (+)-homopilopic acid in high purity. Contaminating (−)-homopilopic acid can be eliminated by treatment with an agent conventionally used for optical resolution such as d-α-methylbenzylamine. From the (+)-homopilopic acid thus obtained, pilocarpine hydrochloride of the same nature as that of the naturally occurring substance may be obtained by known methods.

Typical enzymes which may be mentioned for Process 2 of the present invention include Lipase PS (Amano Pharmaceutical Cp. LTD) derived from Pseudomonas sp., Lipase (Seikagaku Kogyo Co. LTD) derived from *Rhizopus delemar*, Lipozyme IM 20 (Novo Nordisk Bioindustry LTD) derived from *Rhizomucor miehei*, Lipase B from *Pseudomonas fragi* and Lipase OF from from *Candida cylindraceae* (Meito Sangyo Co. LTD), Lipase T-01 (Toyo Jozo Co. LTD) from *Pseudomonas fragi*, Esterase (Boehringer Mannheim) from porcine liver, Cholesterol Esterase T-18 (Toyo Jozo Co. LTD) from Pseudomonas sp., and Lipoprotein Lipase (Wako Pure Chemical Industries Co. LTD) from Pseudomonas sp.

In Process 2 of the invention, the reaction is conducted by dissolving one of the above mentioned enzymes in water or other suitable buffer and contacting with ($\pm$)-homopilopic acid ester. The ratio of the enzyme, ($\pm$)-homopilopic acid ester and the solvent varies depending on the enzyme used, and usually in the range of 1:0.5–1000:2–1,000,000 parts by weight. Preferably the reaction is carried out by shaking at 20°–37° C. for 2–100 hrs. in a phosphate buffer or Tris-HCl at a pH of 5–9, preferably 6.0–8.0, whereby (+)-homopilopic acid is formed in the aqueous solution. The reaction may be facilitated by adding a surface active agent such as Tween 80 to a concentration of 0.02 to 1% by weight. The pH value of the reaction mixture decreases as the formation of (+)-homopilopic acid proceeds and therefore, it is preferable to neutralize and adjust the pH with 0.5N sodium hydroxide, sat. sodium hydrogen carbonate or sat. sodium carbonate. After the reaction, sodium salt of (+)-homopilopic acid can be recovered and purified from the reaction mixture in analogous way as in Process 1, by conventional solvent-extraction, ion exchange chromatography, etc. The ratio of (+)-form and (−)-form of the homopilopic acid recovered by solvent extraction ranges 84:16 to 10:90 depending on the particular enzyme used. (+)-Homopilopic acid can be obtained in best purity by using Paratase M 1000 L(Novo Nordisk Bioindustry LTD). Contaminating (−)-homopilopic acid can be eliminated by treatment with an agent such as d-α-methylbenzylamine conventionally used for optical resolution. From the (+)-homopilopic acid thus obtained, (+)-pilocarpine hydrochloride of the same nature as that of the natural substance may be obtained by means of known techniques (97.5% purity).

Unlike Processes 1 and 2, Process 3 of the present invention does not require the optical resolution step. Process 3 is characterized in that it avoids the complicated step of optical resolution, thus achieving improvement in the yield.

Process 3 comprises the first step of selectively hydrolyzing (−)-homopilopic acid ester in ($\pm$)-homopilopic acid ester to recover (+)-homopilopic acid ester, and the second step of hydrolyzing the recovered (+)-homopilopic acid ester to give (+)-homopilopic acid.

Typical enzymes which may be mentioned for the first step above are Lipase T-01 from *Chromobacterium viscosum* and Cholesterol Esterase T-18 from Pseudomonas sp. (Toyo Jozo Co. LTD), Lipase B (Wako Pure Chemical Industries Co. LTD) from *Pseudomonas fragi*, Lipase PS (Amano Pharmaceutical Co. LTD) derived from Pseudomonas sp., Lipase (Sigma) derived from *Chromobacterium viscosum*, and the like. Typical microorganisms which may used in the first step include *Brevibacterium ammoniagens* IFO 12072, *Escherichia vulneris* JCM 1688, *Rhodotorula rubra* IFO 0893, and the like. The reaction of the first step is performed by dissolving at least one of the the above mentioned enzymes or microorganisms or the treated matters thereof in water or suitable buffer and contacting with ($\pm$)-homopilopic acid ester. The ratio of the enzyme, ($\pm$)-homopilopic acid ester and the solvent varies depending on the enzyme used, and usually in the range of 1:0.5–1000-:2–1,000,000 parts by weight. The reaction may be facilitated by adding a surface active agent such as Tween 80 to a concentration of 0.02 to 1% by weight. Preferably the reaction is carried out by shaking at 20°-37° C. for several hours to 1 week in a phosphate buffer or Tris-HCl at a pH of 5-9, preferably 6.0-8.0, whereby (−)-homopilopic acid is formed in the aqueous layer and (+)-homopilopic acid remains in the oily layer. The reaction period varies depending on the respective types and amounts of the enzyme and the starting ester, and preferably the reaction is stopped when the yield of homopilopic acid produced in the aqueous layer reaches at leat 50% or more. The pH value of the reation mixture decreases as the formation of homopilopic acid proceeds and therefore, it is preferable to adjust the pH to 6-8 with 0.5N sodium hydroxide, sat. sodium hydrogen carbonate or sat. sodium carbonate. After the reaction, the unreacted (+)-homopilopic acid ester can be recovered using an organic solvent such as diethyl ether or ethyl acetate and then used as a starting material in the second step.

Typical enzymes which may be used for the second step are Lipase (Seikagaku Kogyo Co. LTD) derived from *Rhizopus delemar*, Lipozyme IM 20 (Novo Nordisk Bioindustry LTD) derived from *Rhizomucor miehei*, Lipase OF (Meito Sangyo Co. LTD) from *Candida cylindraceae*, Esterase (Boehringer Mannheim) from porcine liver, etc. Suitable microorganisms for the second step are *Aspergillus sojae* IAM 2703, *Escherichia coli* IFO 3366, *Xanthomonas oryzae* IFO 3510, *Candida utilis* IFO 4961, *Pseudomonas aeruginosa* IAM 13130, *Serratia plymuthica* JCM 1244, *Cellulomonas turbata* FERM P-9059, *Nocardia erythropolis* IAM 1484, *Nocardia rubropertincta* JCM 3204, *Bacillus subtilis* IFO 3108, *Flavobacterium lutescens* IFO 3084, *Brevibacterium ketoglutamicum* ATCC 15588, *Mycobacterium rhodochrous* IFO 13161, *Rhizomucor miehei* IFO 9740, *Rhodococcus erythropolis* IFO 12682, and the like. Though (+)-homopilopic acid can be obtained by culturing these microorganisms in a medium containing (+)-homopilopic acid ester, it is preferable to conduct the step using a culture obtained by culturing a microrganism in a medium containing yeast extract, peptone, glucose, mineral salts, and the like, at 20°-37° C. for a period of 1 day to 1 week, or otherwise using cells or a supernatant from the culture, or a treated matter thereof such as crude enzyme solution obtained by disrupting the cells in the culture.

Namely, the reaction of the second step may be effected by dissolving or suspending at least one of the enzymes or microrganisms or a treated matter thereof in water or an appropriate buffer, and contacting the mixture with the unreacted (+)-homopilopic acid ester recovered in the first step. The ratio of the enzyme or enzymatically active substance, (±)-homopilopic acid ester and the solvent varies depending of the nature of the enzyme or microorganism used, and usually in the range of 1:0.5-1000:2-1,000,000 parts by weight. Preferably the reaction is carried out by shaking at 20°-37° C. for 1 to several hours in a phosphate buffer or Tris-HCl at a pH of 5-9 preferably 6.0-8.0, whereby (+)-homopilopic acid is formed in the aqueous solution. The reaction may be facilitated as in the first step by adding a surface active agent or by adjusting the pH value of the reaction mixture to 6-8 with alkaline solution. The completion of the reaction may be monitored by means of HPLC etc. After the reaction, the sodium salt of (+)-homopilopic acid can be recovered and purified from the reaction mixture by conventional methods such as solvent-extraction and ion exchange chromatography. NMR analysis of the methyl ester of the recovered product showed no peak corresponding to (−)-homopilopic acid, indicating that substantially pure (+)-homopilopic acid was formed. From the (+)-homopilopic acid thus obtained, (+)-pilocarpine hydrochloride of the same the nature as that of natural substance may be obtained by known methods.

EFFECT OF THE INVENTION

According to the present invention, the reaction is carried out using a biocatalyst such as an enzyme, a microorganism, etc., and therefore the reaction conditions are so mild that no cleavage of the lactone ring occurs and the yield of (+)-homopilopic acid is very high.

Process 3 of the invention does not necessitate the optical resolution step, leading to a more simple procedure and an increase in the yield. Therefore, the invention contributes largely to the production of pilocarpine hydrochloride useful as an agent for treating glaucoma.

The following non-limiting Examples further illustrate the invention.

In the Examples, NMR data were determined in $CDCl_3$ in the presence of 0.5 equivalent of Eu(hfc){tris-[3-(heptafluoropropylhydroxymethylene)-d-camphor-]europium (III)}.

The following Examples 1-24 illustrate the procedure of Process 1 of the present invention.

EXAMPLE 1

100 ml of the medium as indicated in Table 1 was inoculated with 1 platinum loop of *Nocardia rubropertincta* JCM 3024 strain and cultured for 4 days at 30° C. The resultant culture was centrifuged to remove the supernatant and the pellet (216 mg cells, dry weight) was suspended in 1.9 ml of 0.1M phosphate buffer (pH 7.0). To the suspension, 1 μl of Tween 80 and 92 μl of (±)-homopilopic acid octyl ester were added and allowed to react at 30° C. for 24 hours with stirring. During the reaction, sat. sodium carbonate solution was added every 6 hours to adjust the pH to 7. After the reaction, 23 mg of crystalline homopilopic acid was obtained by solvent-extraction. The content of (+)-homopilopic acid in the product was determined by NMR spectroscopy after conversion into methyl ester thereof, and found to be 87%, while that of (−)-homopilopic acid was 13%.

TABLE 1

| | |
|---|---|
| Nutrient broth | 4 g |
| Yeast extract | 2 g |
| Glucose | 7.5 g |
| $(NH_4)_2SO_4$ | 5 g |
| $Na_2HPO_4.12H_2O$ | 3 g |
| $KH_2PO_4$ | 0.3 g |
| $MgSO_4.7H_2O$ | 0.1 g |
| $CaCl_2.2H_2O$ | 0.05 g |
| $FeSO_4.7H_2O$ | 0.01 g |
| $Na_2MoO_4$ | 0.6 mg |
| $MnSO_4.6H_2O$ | 0.6 mg |
| $ZnSO_4.7H_2O$ | 1.2 mg |

Dissolve in 1 l of water and adjust to pH 7.0.

EXAMPLE 2

100 ml of the medium as indicated in Table 1 was inoculated with 1 platinum loop of *Escherichia coli* IFO 3366 strain and cultured for 1 day at 30° C. The resultant culture was centrifuged to remove the supernatant and the pellet (220 mg in dry weight) was suspended in 1.6 ml of 0.1M Tris (pH 8.0). To the suspension, 1 μl of Tween 80 and 75 μl of (±)-homopilopic acid ethyl ester were added and allowed to react at 30° C. for 24 hours with stirring. During the reaction, sat. sodium carbonate solution was added every 6 hours to adjust the pH to 8. After the reaction, 23 mg of crystalline homopilopic acid was obtained by solvent-extraction. The content of (+)-homopilopic acid in the product was determined by NMR spectroscopy after formation of methyl ester thereof, and found to be 78%, while that of (−)-form was 22%.

EXAMPLE 3

5 ml of the medium as indicated in Table 2 was inoculated with spores of *Rhizomucor miehei* IFO 9740 and cultured for 3 days at 30° C. The resultant culture was transferred to 100 ml of the same medium and cultured for further 4 days at 30° C. The culture thus obtained was filtered to remove the supernatant and the pellet (650 mg cells, dry weight) was suspended in 7.5 ml of 0.1M phosphate buffer (pH 7.0). To the suspension, 3 μl of Span 80 and 200 μl of (±)-homopilopic acid ethyl ester were added and allowed to react at 30° C. for 48 hours with stirring. During the reaction, sat. sodium carbonate solution was added every 6 hours to adjust the pH to 7. After the reaction, 25 mg of crystalline homopilopic acid was obtained by solvent-extraction. The content of (+)-homopilopic acid in the product was determined by NMR spectroscopy after conversion into methyl ester thereof, and found to be 91%, while that of (−)-form was 9%.

TABLE 2

| Yeast extract | 5 g |
|---|---|
| Malt extract | 5 g |
| (NH$_4$)$_2$SO$_4$ | 5 g |
| Sucrose | 10 g |
| MgSO$_4$.7H$_2$O | 0.1 g |
| CaCl$_2$.2H$_2$O | 0.05 g |
| FeSO$_4$.7H$_2$O | 0.01 g |

Dissolve in 1 l of water and adjust to pH 6.0.

EXAMPLES 4-24

In an analogous way as in Examples 1-3, (+)-homopilopic acid was prepared using various types of microorganisms. The results are shown in Table 3.

TABLE 3

| Ex. No. | Strain | Starting[1] Material | Yield (%) | Content[2] (%) |
|---|---|---|---|---|
| 4 | *Arthrobacter globiformis* IFO 12136 | Et | 14 | 62 |
| 5 | *Aspergillus sojae* IAM 2703 | Me | 58 | 52 |
| 6 | *Aspergillus terreus* IAM 2179 | Et | 38 | 43 |
| 7 | *Cunninghamella echinulata* IFO 4443 | Et | 42 | 35 |
| 8 | *Xanthomonas oryzae* IFO 3510 | Et | 35 | 57 |
| 9 | *Xanthomonas campestris* IFO 13303 | Et | 35 | 51 |
| 10 | *Candida utilis* IFO 4961 | Et | 38 | 48 |
| 11 | *Pseudomonas aeruginosa* IAM 1275 | Et | 36 | 77 |
| 12 | *Serratia plymuthica* JCM 1244 | Et | 21 | 67 |
| 13 | *Cellulomonas turbata* FERM P-9059 | Et | 31 | 53 |
| 14 | *Nocardia erythropolis* IAM 1484 | tBu | 25 | 79 |
| 15 | *Nocardia opaca* IAM 12123 | Et | 41 | 49 |
| 16 | *Nocardia corallina* IAM 12121 | Et | 36 | 75 |
| 17 | *Nocardia rubropertincta* JCM 3204 | Oct | 40 | 89 |
| 18 | *Bacillus subtilis* IFO 3108 | Et | 38 | 79 |
| 19 | *Flavobacterium lutescens* IFO 3084 | Et | 36 | 67 |
| 20 | *Brevibacterium ketoglutamicum* ATCC 15588 | Et | 33 | 64 |
| 21 | *Mycobacterium rhodochrous* IFO 13161 | Et | 25 | 71 |
| 22 | *Rhizomucor miehei* IFO 9740 | Oct | 50 | 80 |
| 23 | *Rhodococcus erythropolis* IFO 12682 | Et | 37 | 69 |
| 24 | *Rhodotorula rubra* IFO 0383 | iPr | 65 | 26 |

[1]Starting ester: (±)-homopilopic acid methyl ester (Me), ethyl ester (Et), isoporpyl ester (iPr), t-butyl ester (tBu), octyl ester (Oct).
[2]Content (%): [(+)-Homopilopic acid/total homopilopic acid produced] × 100

EXAMPLE 25

36 mg of Lipase (Seikagaku Kogyo) derived from *Rhizopus delemar* was suspended in 2 ml of 0.1M phosphate buffer (pH 7.0), 1 μl of Tween 80 and 100 mg of (±)-homopilopic acid ethyl ester were added and the mixture was allowed to react at 30° C. for 24 hours with stirring. During the reaction, sat. sodium carbonate solution was added every 6 hours to adjust the pH to 7. After the reaction, 19 mg of white needles of homopilopic acid were obtained by solvent-extraction (Yield, 16%). The content of (+)-homopilopic acid in the product was determined by NMR spectroscopy after formation of methyl ester thereof, and found to be 69%, while that of (−)-form was 31%.

EXAMPLE 26

60 U of Esterase (1000 U/ml, Boehringer Mannheim) from porcine liver was suspended in 2 ml of 0.1M phosphate buffer (pH 7.0), 1 μl of Tween 80 and 100 mg of (±)-homopilopic acid butyl ester were added and the mixture was allowed to react at 30° C. for 24 hours with stirring. During the reaction, sat. sodium carbonate solution was added every 6 hours to adjust the pH to 7. After the reaction, 30 mg of crystalline homopilopic acid was obtained by solvent-extraction (Yield, 25%). The content of (+)-homopilopic acid in the product was determined by NMR spectroscopy after formation of methyl ester thereof, and found to be 71%, while that of (−)-form was 29%.

EXAMPLE 27-35

In an analogous way as in Examples 25-26, (+)-homopilopic acid was prepared using various types of enzymes. The results are shown in Table 4.

TABLE 4

| Ex. No. | Enzyme | Starting ester[*1] (mg) | Enzyme (mg) | Solvent[*2] (ml) | Reaction time (hr) | Yield (%) | Content[*3] (%) |
|---|---|---|---|---|---|---|---|
| 27 | Lipase OF (Meito) | 2200 (Me) | 400 | 8 | 24 | 24 | 54 |
| 28 | Lipase IM 20 (Novo) | 132 (Et) | 30 | 1 | 24 | 42 | 73 |
| 29 | Paratase M 1000L | 132 (Et) | 50 | 1 | 24 | 16 | 84 |
| 30 | Lipoprotein lipase | 132 (Oct) | 13 | 1 | 24 | 13 | 40 |
| 31 | Lipoprotein lipase | 132 (iPr) | 13 | 1 | 24 | 11 | 38 |
| 32 | Lipase T-01 (Toyo Jozo) | 220 (Et) | 7 | 10 | 20 | 45 | 17 |
| 33 | Cholesterol esterase T18 (Toyo Jozo) | 220 (Et) | 7 | 10 | 20 | 52 | 10 |
| 34 | Lipase P (Amano) | 1320 (Et) | 200 | 20 | 88 | 55 | 14 |
| 35 | Lipase B (Wako) | 672 (Et) | 9 | 10 | 19 | 55 | 17 |

[*1]Starting ester: (±)-Homopilopic acid methyl ester (Me), ethyl ester (Et), isopropyl ester (iPr) and octyl ester (Oct)
[*2]0.1M Phosphate buffer (pH 7.0)
[*3]Content (%): [(+)-Homopilopic acid/Total homopilopic acid produced] × 100

The following Examples illustrate the preparation according to Process 3 of the present invention.

NMR spectra were determined at 90 MHz, and specific rotation ($[\alpha]_D$) was determined in chloroform at room temperature.

EXAMPLE 36

8.5 mg of Lipase B (Wako) derived from *Pseudomonas fragi* was suspended in 10 ml of 0.1M phosphate buffer (pH 7.0), 4 μl of Tween 80 and 600 mg of (±)-homopilopic acid ethyl ester were added, and the mixture was allowed to react at 30° C. with stirring. During the reaction, sat. sodium carbonate solution was added every 6 hours to adjust the pH to 7. After 19 hours reaction, the pH of the reaction mixture was adjusted to 8.0, 10 ml of diethyl ether was added, vigourously agitated and centrifuged to recover ether phase. This extraction procedure was repeated thrice, and from the combined ether extracts was recovered 235 mg (39%) of (+)-homopilopic acid ethyl ester. $[\alpha]_D$:76.1°.

EXAMPLE 37

235 mg of the recovered ester as obtained in Example 36 was hydrolyzed in the presence of 3 μl of Tween 80, 150 mg of Lipase OF and 12 ml of 0.1M phosphate buffer (pH 7.0). 127 mg of crystalline homopilopic acid was obtained by solvent-extraction. The overall yield through steps 1 and 2 of homopilopic acid was 25%. $[\alpha]_D$:79.4°. The NMR spectroscopy of the product after formation of methyl ester thereof showed substantially no signal for (−)-homopilopic acid methyl ester (FIG. 1).

EXAMPLE 38

A culture of *Bacillus subtilis* IFO 3108 was prepared. 100 ml of the medium as indicated in Table 5 was inoculated with 1 platinum loop of *Bacillus subtilis* IFO 3108. To elevate ester decomposing activity, soybean oil was added to a concentration of 1%, and cultured at 30° C. for 1 day. The resultant culture was centrifuged to give a pellet (360 mg cells, dry weight).

TABLE 5

| Nutrient broth | 4 g |
|---|---|
| Yeast extract | 2 g |
| Glucose | 7.5 g |
| (NH$_4$)$_2$SO$_4$ | 5 g |
| Na$_2$HPO$_4$.12H$_2$O | 3 g |
| KH$_2$PO$_4$ | 0.3 g |
| MgSO$_4$.7H$_2$O | 0.1 g |
| CaCl$_2$.2H$_2$O | 0.05 g |
| FeSO$_4$.7H$_2$O | 0.01 g |
| Na$_2$MoO$_4$ | 0.6 mg |
| MnSO$_4$.6H$_2$O | 0.6 mg |

TABLE 5-continued

| ZnSO$_4$.7H$_2$O | 1.2 mg |
|---|---|

Dissolve in 1 l of water and adjust to pH 7.0.

EXAMPLE 39

360 mg (dry weight) of the pellet of *Bacillus subtilis* IFO 3108 as obtained in Example 38 was suspended in 5 ml of 0.1M phosphate buffer (pH 7.0), and 100 mg of (+)-homopilopic acid ethylester as obtained in Example 36 and 2 μl of Tween 80 were added and allowed to react with stirring at 30° C. During the reaction, sat. sodium carbonate solution was added every 6 hours to adjust the pH to 7. After 72 hours reaction, 71 mg of homopilopic acid was obtained as white needles by solvent-extraction (Yield, 84%). $[\alpha]_D$:81.2°.

EXAMPLE 40

A culture of *Rhizomucor miehei* IFO 9740 was prepared. 5 ml of the medium as indicated in Table 6 was inoculated with spores of *Rhizomucor miehei* IFO 9740 and cultured at 30° C. for 3 days. The resultant culture was used to inoculate 100 ml of the same medium and cultured for further 4 days at 30° C. The culture was filtrated to remove the supernatant and 920 mg (dry weight) of the cells was obtained.

TABLE 6

| Yeast extract | 5 g |
|---|---|
| Malt extract | 5 g |
| (NH$_4$)$_2$SO$_4$ | 5 g |
| Sucrose | 10 g |
| MgSO$_4$.7H$_2$O | 0.1 g |
| CaCl$_2$.2H$_2$O | 0.05 g |
| FeSO$_4$.7H$_2$O | 0.01 g |

Dissolve in 1 l of water and adjust to pH 6.0.

EXAMPLE 41

100 mg of (+)-homopilopic acid ethylester as obtained in Example 36, 200 mg of the cultured strain of *Rhizomucor miehei* IFO 9740 as obtained in Example 40 and 2 μl of Tween 80 were added to 5 ml of 0.1M phosphate buffer (pH 7.0), and allowed to react at 30° C. During the reaction, sat. sodium carbonate solution was added every 6 hours in order to adjust the pH to 7. After 68 hours reaction, 61 mg of crude crystalline homopilopic acid was obtained by solvent-extraction (Yield, 72%). $[\alpha]_D$:79.8°. NMR spectroscopy of the product after formation of methyl ester showed substantially no signal of (−)-homopilopic acid methyl ester.

EXAMPLES 42-45

(+)-Homopilopic acid ester was recovered using 4 types of enzymes which selectively act on (−)-homopilopic acid ester. The reaction was conducted in 10 ml of 0.1M phosphate buffer (pH 7.0) at 30° C. The results are shown in Table 7.

TABLE 7

| Ex. No. | Enzyme | (First Step) | | | |
|---|---|---|---|---|---|
| | | Enzyme (mg) | Starting ester*[1] (mg) | Reaction time (hr) | Recovery of ester (%) | Specific rotation $[\alpha]_D$ |
| 42 | Lipase T-01 (Toyo Jozo) | 7 | 200 (Et) | 30 | 28 | 74.1 |
| 43 | Cholesterol esterase T18 (Toyo Jozo) | 7 | 200 (Et) | 20 | 40 | 73.2 |
| 44 | Lipase (Sigma) | 4 | 300 (Oct) | 14 | 28 | 75.0 |
| 45 | Lipase PS (Amano) | 50 | 600 (Et) | 55 | 48 | 74.4 |

*[1]Et: (±)-Homopilopic acid ethyl ester, (Oct): (±)-Homepilopic acid octylester

EXAMPLES 46-47

(+)-Homopilopic acid ester as recovered in Example 44 was hydrolyzed using various enzymes as indicated in Table 8. The reaction was conducted in 5 ml of 0.1M phosphate buffer (pH 7.0) at 30° C. The results are shown in Table 8.

TABLE 8

| Ex. No. | Enzyme | (Second step) | | | | |
|---|---|---|---|---|---|---|
| | | Enzyme (mg) | Starting ester*[1] (mg) | Reaction time (hr) | Yield*[2] (%) | Specific rotation $[\alpha]_D$ |
| 46 | Lipase (Seikagaku Kogyo) | 20 | 50 | 45 | 88 | 79.3 |
| 47 | Esterase (Boehringer) | 10 (Unit) | 50 | 45 | 89 | 80.5 |
| 48 | Lipozyme IM 20 (Novo) | 10 | 50 | 50 | 92 | 81.5 |
| 49 | Lipase OF (Meito) | 20 | 50 | 55 | 94 | 78.1 |

*[1]Examples 46 and 47: the recovered ester of Ex. 44 was used. Examples 48 and 49: the recovered ester of Ex. 45 was used.
*[2]Yield of homopilopic acid.

EXAMPLES 48-49

(+)-Homopilopic acid ethyl ester as recovered in Example 45 was hydrolyzed as in Examples above using various enzymes acting on (+)-homopilopic acid ester. The results are shown in Table 8.

EXAMPLES 50-52

110 mg of (+)-homopilopic acid ethyl ester as recovered in Example 42 was hydrolyzed using various enzymes acting on (+)-homopilopic acid ester. The reaction was conducted in 5 ml of 0.1M phosphate buffer (pH 7.0) at 30° C. for 48 hours. The results are shown in Table 9.

TABLE 9

| Ex. No. | Strain | (Second Step, using microorganism) | | |
|---|---|---|---|---|
| | | Dry weight of microorganism (mg) | Starting*[1] ester | Yield (%) |
| 50 | Aspergillus sojae IAM 2703 | 32 | Et | 36 |
| 51 | Escherichia coli IFO 3366 | *[2] | Et | 68 |
| 52 | Xanthomonas oryzae IFO 3510 | 42 | Et | 12 |
| 53 | Candida utilis IFO 4961 | 23 | Et | 8 |
| 54 | Pseudomonas aeruginosa IFO 13130 | 30 | Et | 10 |
| 55 | Serratia plymuthica JCM 1244 | 13 | Et | 14 |
| 56 | Cellulomonas turbata FERM P-9059 | 17 | Et | 60 |
| 57 | Nocardia erythropolis IAM 1484 | 18 | Et | 14 |
| 58 | Nocardia rubropertincta JCM 3204 | 43 | Et | 4 |
| 59 | Flavobacterium lintercens IFO 3084 | 20 | Et | 29 |
| 60 | Brevibacterium ketoglutaricum ATCC 15588 | 16 | Et | 59 |
| 61 | Rhodococcus erythropolis IFO 12682 | 18 | Et | 33 |
| 62 | Mycobacterium rhodochrous IFO 13161 | 6 | Oct | 6 |

*[1]Et: (±)-Homopilopic acid ethylester, Oct: (±)-octyl ester. In Ex. No. 50~52, 53–58, 59–61 and 62, esters recovered in Examples 42, 43, 45 and 44 were used, respectively.
*[2]After culturing in the medium as shown in Table 1 at 30° C. for 24 hrs., the recovered ester (110 mg) was added and allowed to react for 48 hrs.

EXAMPLES 53-58

(+)-Homopilopic acid ethyl ester as recovered in Example 43 was hydrolyzed as in Examples above using various enzymes. The results are shown in Table 9.

EXAMPLES 59-61

(+)-Homopilopic acid ethyl ester as recovered in Example 45 was hydrolyzed as in Examples above using various enzymes. The results are shown in Table 9.

EXAMPLE 62

(+)-Homopilopic acid octyl ester as recovered in Example 44 was hydrolyzed as in Examples above using the enzyme as indicated in Table 9. The results are shown in Table 9.

Following Examples 63-65 illustrate the preparation of the culture to be used in the first step of Process 3.

EXAMPLE 63

*Brevibacterium ammoniagens* IFO 12072 strain was cultured in 100 ml of the medium as indicated in Table 5 at 30° C. for 1 day to produce 270 mg (dry weight) of the cells.

EXAMPLE 64

*Escherichia vulneris* JCM 1688 strain was cultured in 100 ml of the medium as indicated in Table 5 at 30° C. for 1 day to produce 540 mg (dry weight) of the cells.

EXAMPLE 65

*Rhodotorula rubra* IFO 0893 strain was cultured in 100 ml of the medium as indicated in Table 6 at 30° C. for 2 day to produce 750 mg (dry weight) of the cells.

EXAMPLES 66-68

These examples illustrate the preparation of (+)-homopilopic acid by the combination of the first step using the cells as obtained in Examples 63-65 and the second step using the recovered (+)-homopilopic acid ester and Lipase OF. The results are shown in Table 10.

TABLE 10

| Ex. No. | First step*1 | | Second step*2 | | Specific rotation of the product [α]$_D$ |
|---|---|---|---|---|---|
| | Microorganism (mg) | Recovered ester (mg) | Lipase OF | Yield (%)*3 | |
| 66 | 270 | 30 | 50 | 28 | 80.3 |
| 67 | 540 | 28 | 40 | 25 | 79.8 |
| 68 | 750 | 25 | 30 | 25 | 78.9 |

*1 0.1M Tris (pH 7.5): 2 ml, (±)-Homopilopic acid ethylester: 100 mg, 30° C., 50 hours.
*2 0.1M Tris (pH 7.5): 1 ml, Lipase OF, 30° C., 50 hours.
*3 Yield of homopilopic acid.

What is claimed is:

1. A process for preparing (+)-homopilopic acid and salts thereof, which comprises hydrolyzing a mixture of (+)-homopilopic acid ester of the general formula (I):

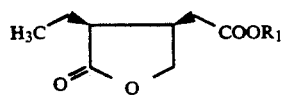

[I]

wherein $R_1$ denotes a straight or branched $C_1$-$C_{10}$ hydrocarbon, and (−)-homopilopic acid ester of the general formula (II):

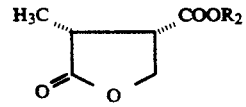

[II]

wherein $R_2$ denotes a straight or branched $C_1$-$C_{10}$ hydrocarbon, in the presence of a microorganism selected from the group consisting of *Escherichia coli* IFO 3366, *Nocardia rubropertincta* FERM BP-3641, *Bacillus subtilis* IFO 3108, *Brevibacterium ketoglutamicum* ATCC 15588, and *Rhizomucor miehei* IFO 9740, or a crude enzyme solution thereof obtained by disrupting cells of said microorganism wherein said crude enzyme solution contains at least one enzyme selected from the group consisting of a lipase, an esterase, a cholesterol esterase, and a lipoprotein lipase.

2. A process for preparing (+)-homopilopic acid and salts thereof, which comprises hydrolyzing a mixture of (+)-homopilopic acid ester of the general formula (I):

[I]

wherein $R_1$ denotes a straight or branched $C_1$-$C_{10}$ hydrocarbon, and (−)-homopilopic acid ester of the general formula (II):

[II]

wherein $R_2$ denotes a straight or branched $C_1$-$C_{10}$ hydrocarbon, using at least one enzyme selected from the group consisting of a lipase, an esterase, a cholesterol esterase, and a lipoprotein lipase.

3. A process for preparing (+)-homopilopic acid and salts thereof, which comprises, in a first step, hydrolyzing a mixture of (+)-homopilopic acid ester of the general formula (I):

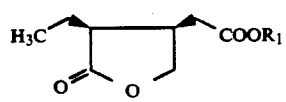

[I]

wherein $R_1$ denotes a straight or branched $C_1$-$C_{10}$ hydrocarbon, and (−)-homopilopic acid ester of the general formula (II):

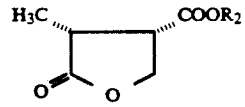

[II]

wherein $R_2$ denotes a straight or branched $C_1$-$C_{10}$ hydrocarbon, using either a hydrolase selected from the group consisting of a lipase, an esterase, and a cholesterol esterase, or a microorganism selected from the group consisting of *Brevibacterium ketoglutamicum* ATCC 1588 and *Escherichia coli* IFO 3366, or a crude enzyme solution thereof obtained by disrupting cells of said microorganism wherein said crude enzyme solution contains at least one enzyme selected from the group consisting of a lipase, an esterase, a cholesterol esterase, and a lipoprotein lipase, recovering the unreacted (+)-homopilopic acid ester, and thereafter, in a second step, hydrolyzing said unreacted (+)-homopilopic acid ester using either a hydrolase selected from a lipase or an esterase, or a microorganism selected from the group consisting of *Escherichia coli* IFO 3366, *Nocardia rubropertincta* FERM BP-3641, *Bacillus subtilis* IFO 3108, *Brevibacterium ketoglutamicum* ATCC 15588, and *Rhizomucor miehei* IFO 9740, or a crude enzyme solution thereof obtained by disrupting cells of said microorganism wherein said crude enzyme solution contains at least one enzyme selected from the group consisting of a lipase, an esterase, a cholesterol esterase, and a lipoprotein lipase.

4. The process according to any one of claims 1-3, wherein said straight or branched $C_1$-$C_{10}$ hydrocarbon is selected from the group consisting of methyl, ethyl, isopropyl, t-butyl, and octyl.

5. The process of claim 1, wherein said hydrolyzing is carried out by contacting said mixture of homopilopic acid esters with a culture, cells, culture supernatant, or a crude enzyme solution obtained by disrupting cells of said microorganism.

6. The process of claim 1, wherein said microorganism is *Rhizomucor miehei* IFO 9740.

7. The process of claim 2, wherein said enzyme is selected from the group consisting of Lipase PS derived from Pseudomonas sp., Lipase derived from *Rhizopus delemar*, Lipozyme IM 20 derived from *Rhizomucor miehei*, Lipase B from *Pseudomonas fragi*, Lipase OF from *Candida cylindraceae*, Lipase T-01 from *Pseudomonas fragi*, Esterase from procine liver, Cholesterol Esterase T-18 from Pseudomonas sp., and Lipoprotein Lipase from Pseudomonas sp.

8. The process of claim 2, wherein said enzyme is dissolved in a solvent and the ratio of said enzyme: ($\pm$)-homopilopic acid ester: solvent is in the range 1:0.5-1000:2-1,000,000 parts by weight.

9. The process of claim 2, further comprising adding a surface active agent to said mixture of (+)-homopilopic acid ester of general formula (I) and (−)-homopilopic acid ester of general formula (II), and hydrolyzing said mixture.

10. The process of claim 9, wherein said surface active agent is present at a concentration of 0.02 to 1% by weight.

11. The process of claim 9, wherein said surface active agent is Tween 80.

12. The process of claim 2, wherein said enzyme is Paratase M 1000 L.

13. The process of claim 3, wherein said hydrolase employed in the first step is selected from the group consisting of Lipase T-01 from *Chromobacterium viscosum*, Cholesterol Esterase T-18 from Pseudomonas sp., Lipase B from *Pseudomonas fragi*, Lipase PS derived from Pesudomonas sp., and Lipase derived from *Chromobacterium viscosum*.

14. The process of claim 3, wherein said enzyme is dissolved in a solvent and the ratio of said enzyme: ($\pm$)-homopilopic acid ester:solvent is in the range 1:0.5-1000:2-1,000,000 parts by weight.

15. The process of claim 3, further comprising adding a surface active agent to said mixture of (+)-homopilopic acid ester of general formula (I) and (−)-homopilopic acid ester of general formula (II) and hydrolyzing said mixture in said first step, and thereafter hydrolyzing said unreacted (+)-homoplopic acid ester via the use of either said hydrolase, said microorganism, or said crude enzyme solution thereof obtained by disrupting cells of said microorganism wherein said crude enzyme solution contains at least one enzyme selected from the group consisting of a lipase, an esterase, a cholesterol esterase, and a lipoprotein lipase, in the presence of said surface active agent in said second step.

16. The process of claim 15, wherein said surface active agent is present at a concentration of 0.02 to 1% by weight.

17. The process of claim 16, wherein said surface active agent is Tween 80.

18. The process of claim 3, wherein said unreacted (+)-homopilopic acid ester is recovered after said first step via the use of an organic solvent.

19. The process of claim 18, wherein said organic solvent is diethyl ether or ethyl acetate.

20. The process of claim 3, wherein said hydrolase employed in the second step is selected from the group consisting of Lipase derived from *Rhizopus delemar*, Lipozyme IM 20 derived from *Rhizomucor miehei*, Lipase OF from *Candida cylindraceae*, and Esterase from porcine liver.

21. The process of claim 3, wherein said hydrolyzing is carried out by contacting said unreacted (+)-homopilopic acid ester with a culture, cells, culture supernatant, or a crude enzyme solution obtained by disrupting cells of said microorganism wherein said crude enzyme solution contains at least one enzyme selected from the group consisting of a lipase, an esterase, a cholesterol esterase, and a lipoprotein lipase.

22. The process of claim 3, wherein said enzyme is dissolved in a solvent and the ratio of said hydrolase or said crude enzyme solution ($\pm$)-homopilopic acid ester: solvent is in the range 1:0.5-1000:2-1,000,000 parts by weight.

23. The process of claim 15, wherein said hydrolyzing in said second step is facilitated by adjusting the pH of the reaction mixture to between 6-8 with an alkaline solution rather than by employing a surface active agent.

* * * * *